US00PP31934P2

(12) United States Plant Patent
Plocher

(10) Patent No.: US PP31,934 P2
(45) Date of Patent: Jul. 7, 2020

(54) GRAPE PLANT NAMED 'TP 1-1-12'

(50) Latin Name: ***Vitis* interspecific hybrid**
Varietal Denomination: TP 1-1-12

(71) Applicant: Thomas Alan Plocher, Hugo, MN (US)

(72) Inventor: Thomas Alan Plocher, Hugo, MN (US)

( * ) Notice: Subject to any disclaimer, the term of this patent is extended or adjusted under 35 U.S.C. 154(b) by 0 days.

(21) Appl. No.: 16/602,153

(22) Filed: Aug. 16, 2019

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 6/88; A01H 5/08
See application file for complete search history.

*Primary Examiner* — Keith O. Robinson
(74) *Attorney, Agent, or Firm* — Michelle Bos Legal LLC

(57) ABSTRACT

'TP 1-1-12' is a late-budding grape plant notable for its cold hardiness and large cluster size, and the suitability of its fruit for the production of red wine.

10 Drawing Sheets

Latin name: *Vitis* interspecific hybrid.
Variety denomination: 'TP 1-1-12'.

BACKGROUND OF THE VARIETY

'TP 1-1-12' is a new and distinct variety of grape plant selected from a group of seedlings obtained from a controlled cross of female parent 'Troubador' (not patented) and male parent 'E.S. 5-4-16' (not patented) carried out at Hugo, Minn. in 1997. Seedling 'TP 1-1-12' was planted in 1998 and was later selected for its excellent winter hardiness and large fruit cluster size, and the suitability of its fruit for the production of red wine. Asexual propagation by dormant hardwood cuttings was first carried out in 2004 at Hugo, Minn.; subsequent asexual propagations have shown the variety to be stable and to reproduce true to type through successive generations.

BRIEF DESCRIPTION OF THE VARIETY

'TP 1-1-12' is a late-budding grape plant notable for its cold hardiness and large fruit cluster size, and the suitability of its fruit for the production of red wine. A comparison of 'TP 1-1-12' to its parents is shown in Table 1 below.

TABLE 1

Comparison of 'TP 1-1-12' to Parent Varieties

| | 'TP 1-1-12' | 'Troubador' | 'E.S. 5-4-16' |
|---|---|---|---|
| Winter hardiness | Primary bud hardiness to −36° C. | Primary bud hardiness to −40° C. | Primary bud hardiness to −35° C. |
| Bud break | Much later than 'Troubador'; similar to 'E.S. 5-4-16' | Earlier | Similar |
| Acidity at harvest | 0.8% | 1.4% | 0.7% |
| pH | 3.3 to 3.4 | 3.1 | 3.5 |
| Vigor | Less vigorous than either parent | Much more vigorous | More vigorous |

TABLE 1-continued

Comparison of 'TP 1-1-12' to Parent Varieties

| | 'TP 1-1-12' | 'Troubador' | 'E.S. 5-4-16' |
|---|---|---|---|
| Skin tannins | Somewhat higher concentration than 'Troubador'; much higher concentration than E.S. 5-4-16 | Somewhat lower concentration | Much lower concentration |
| Berry size | 12 mm | 8 mm | 15 mm |
| Cluster size | 160 g | 45 g | 200 to 400 g |

A comparison of 'TP 1-1-12' to 'Crimson Pearl' (U.S. Plant Pat. No. 30,263), a related cold-hardy variety, is shown in Table 2 below.

TABLE 2

Comparison of T.P. 1-1-12 to 'Crimson Pearl'.

| | 'TP 1-1-12' | 'Crimson Pearl' |
|---|---|---|
| Winter hardiness | Similar hardiness | Similar |
| Bud break | Slightly earlier | Slightly later |
| Acidity at harvest | 0.8% | 0.7% |
| Vigor | Moderate | Moderate |
| Skin tannins | Higher concentration | Lower concentration |
| Harvest | 9 days Earlier | 9 days Later |

BRIEF DESCRIPTION OF THE PHOTOGRAPHS

The photographs, taken during the 2016, 2018 and 2019 growing seasons at Hugo, Minn., show selected characteristics of 2- and 3-year-old 'TP 1-1-12' grape plants grown on their own roots.

Figure 1:
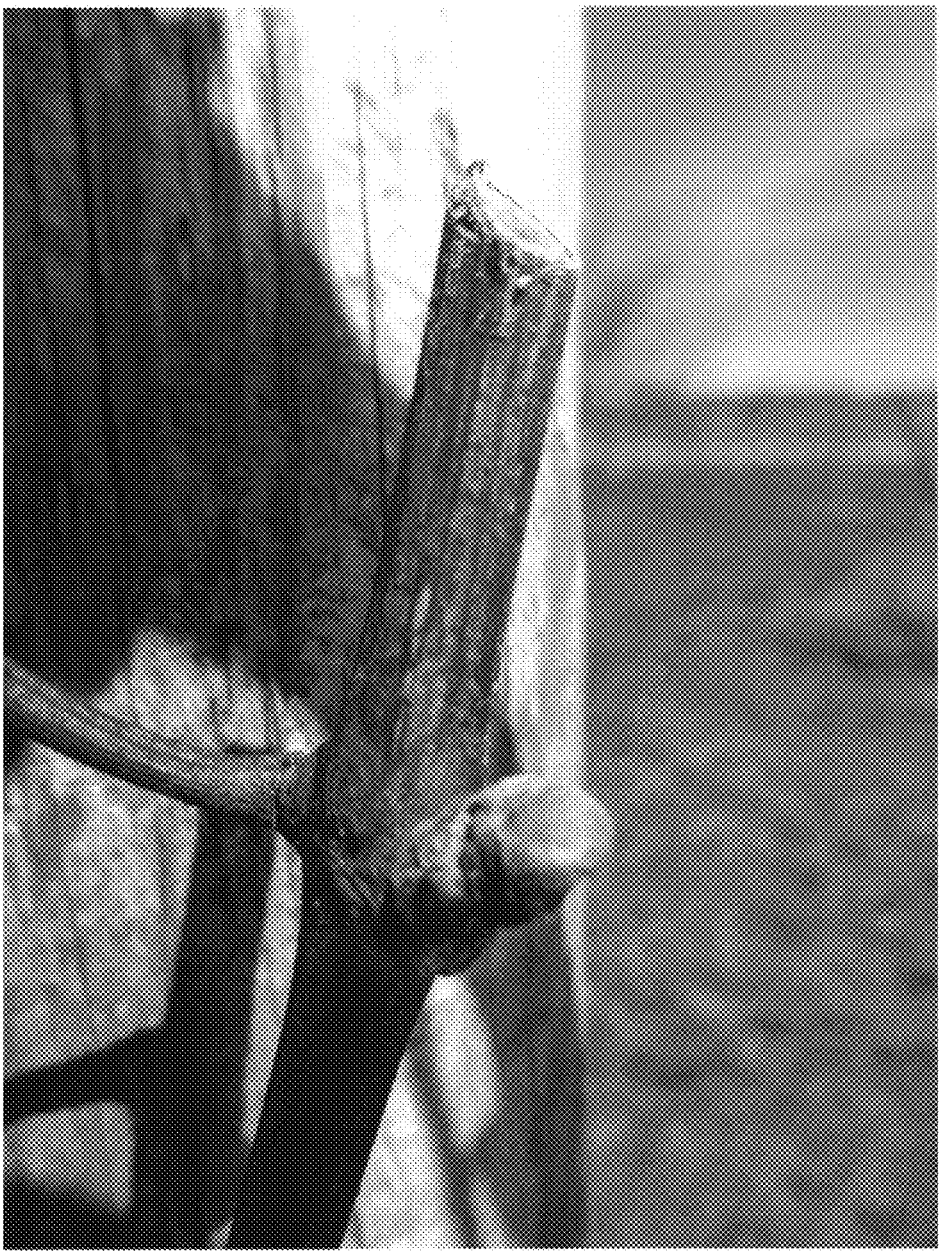
Figure 2:
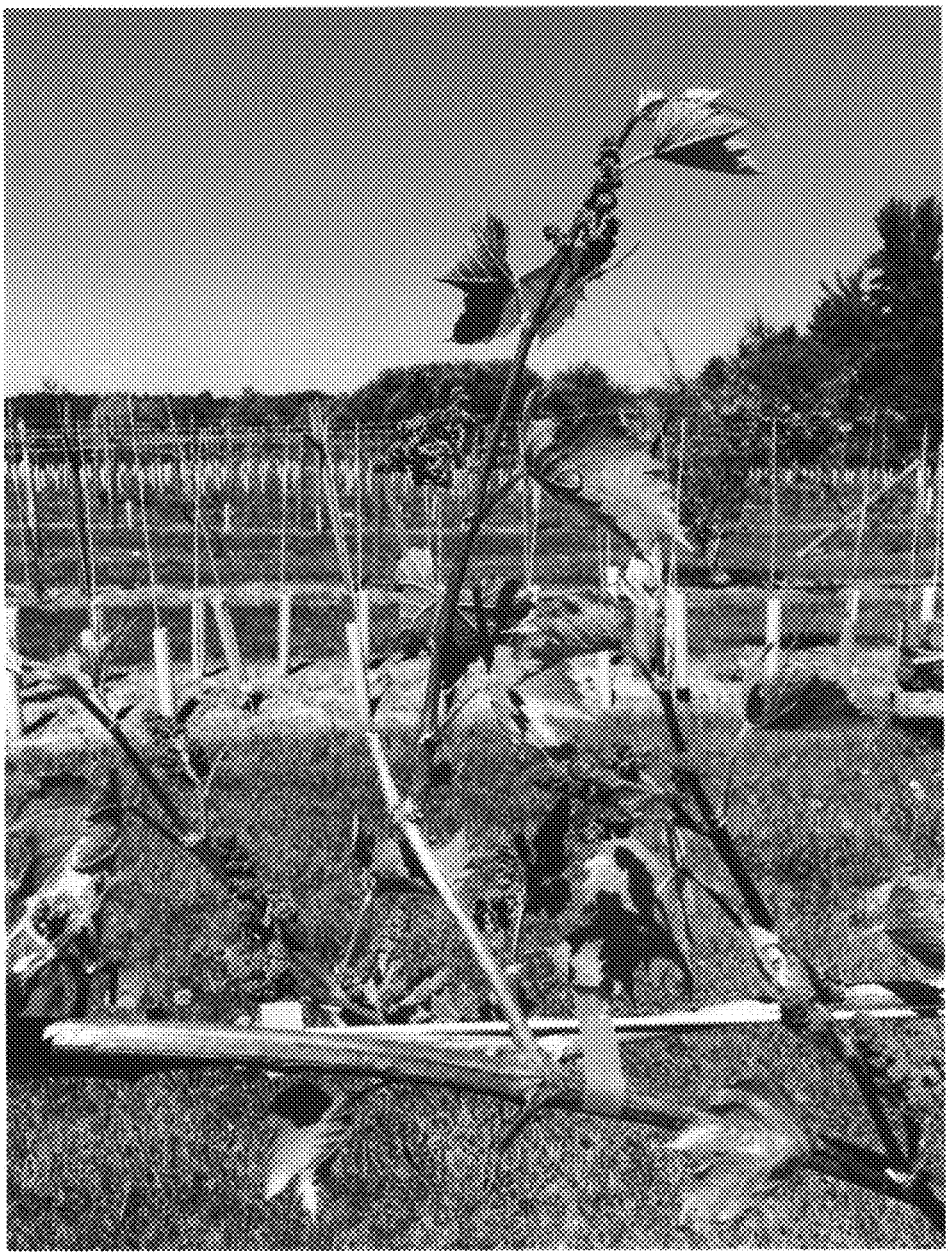
Figure 3:
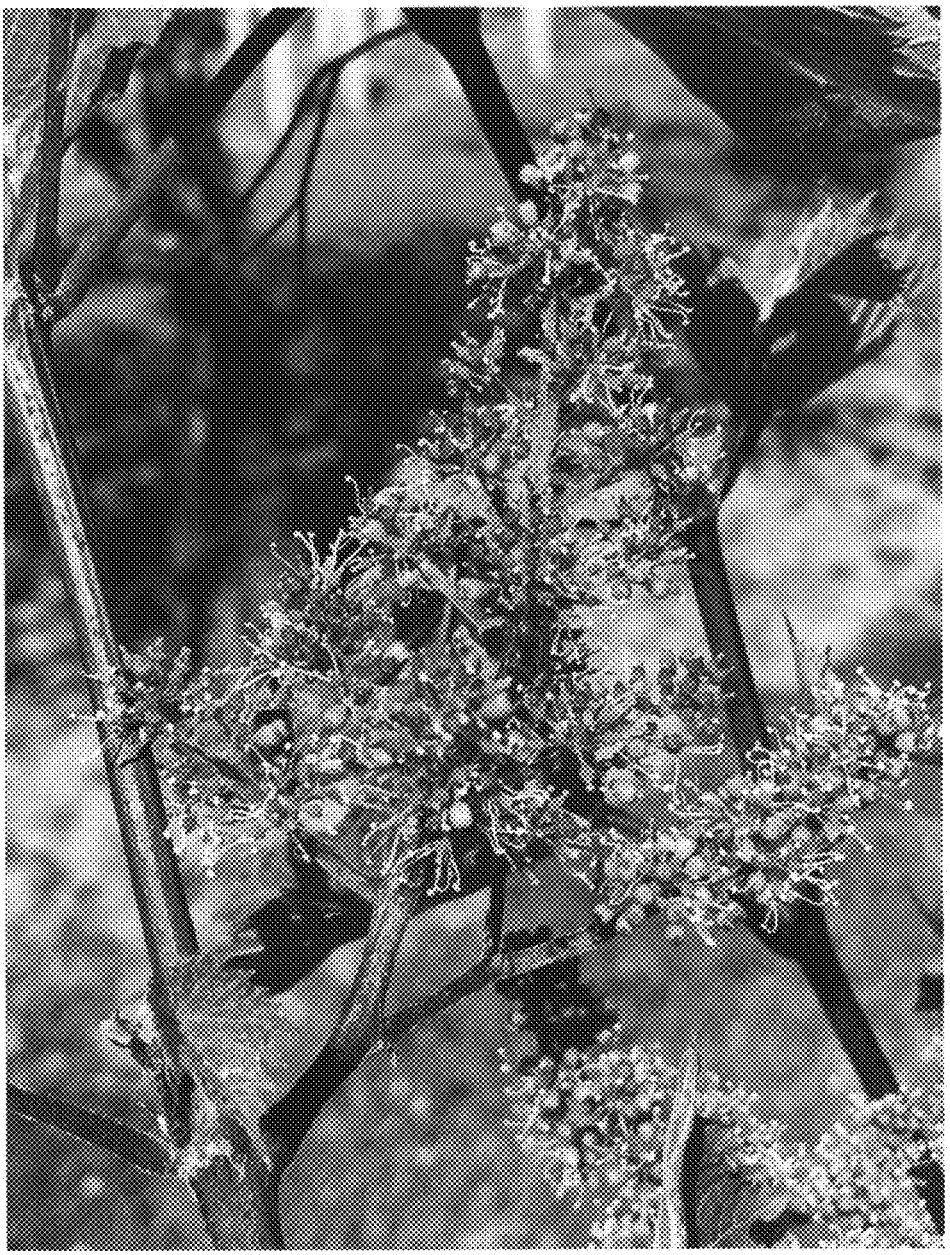
Figure 4:
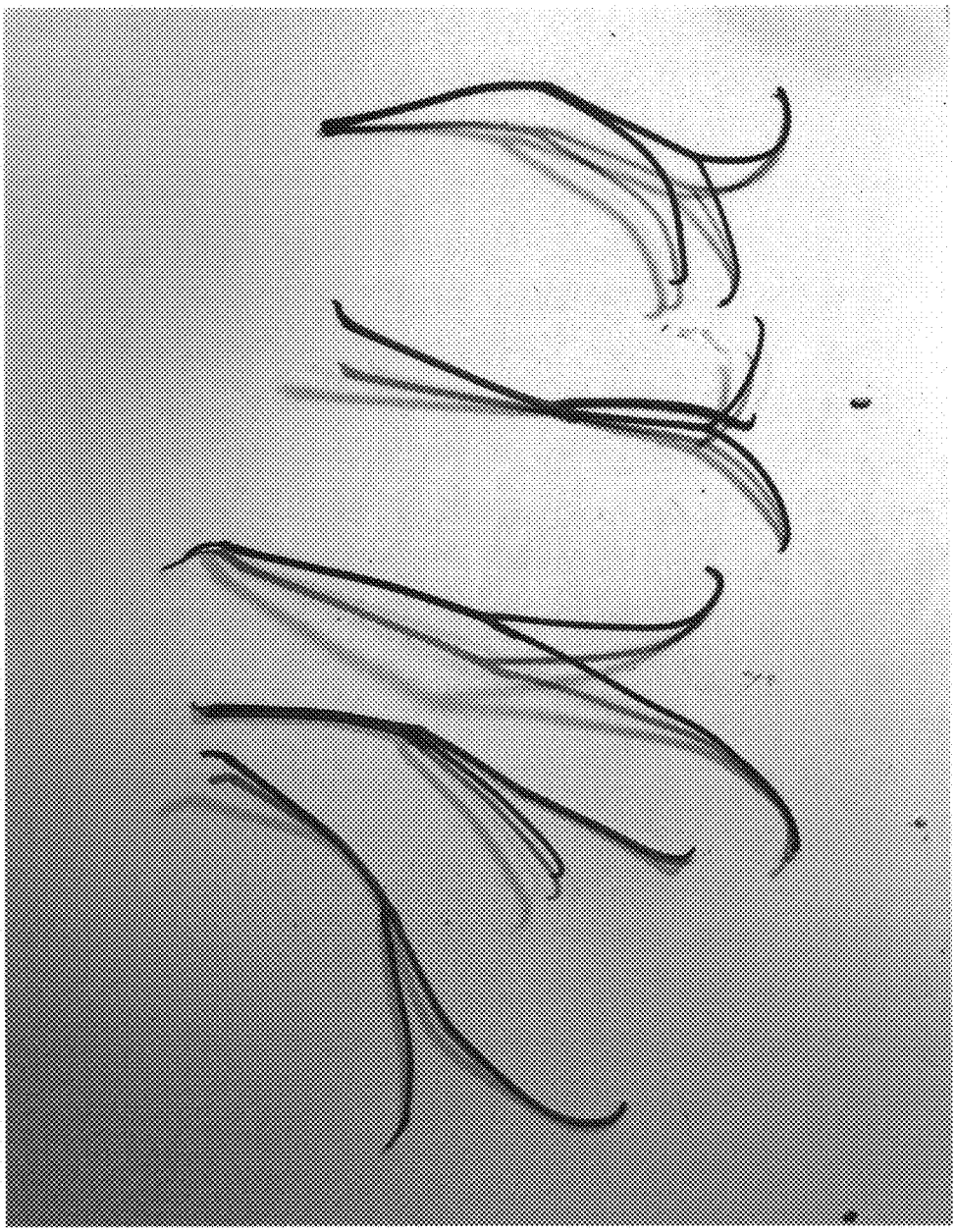
Figure 5:
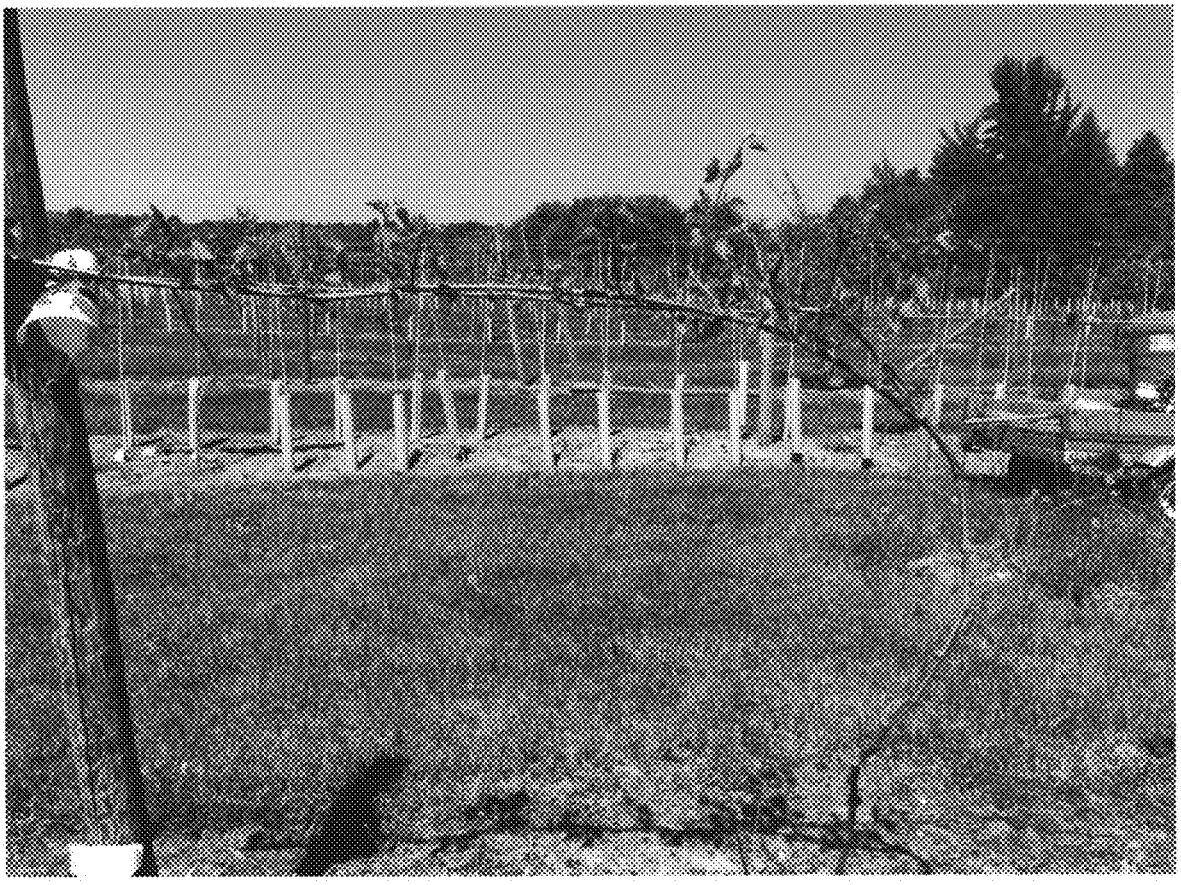
Figure 6:
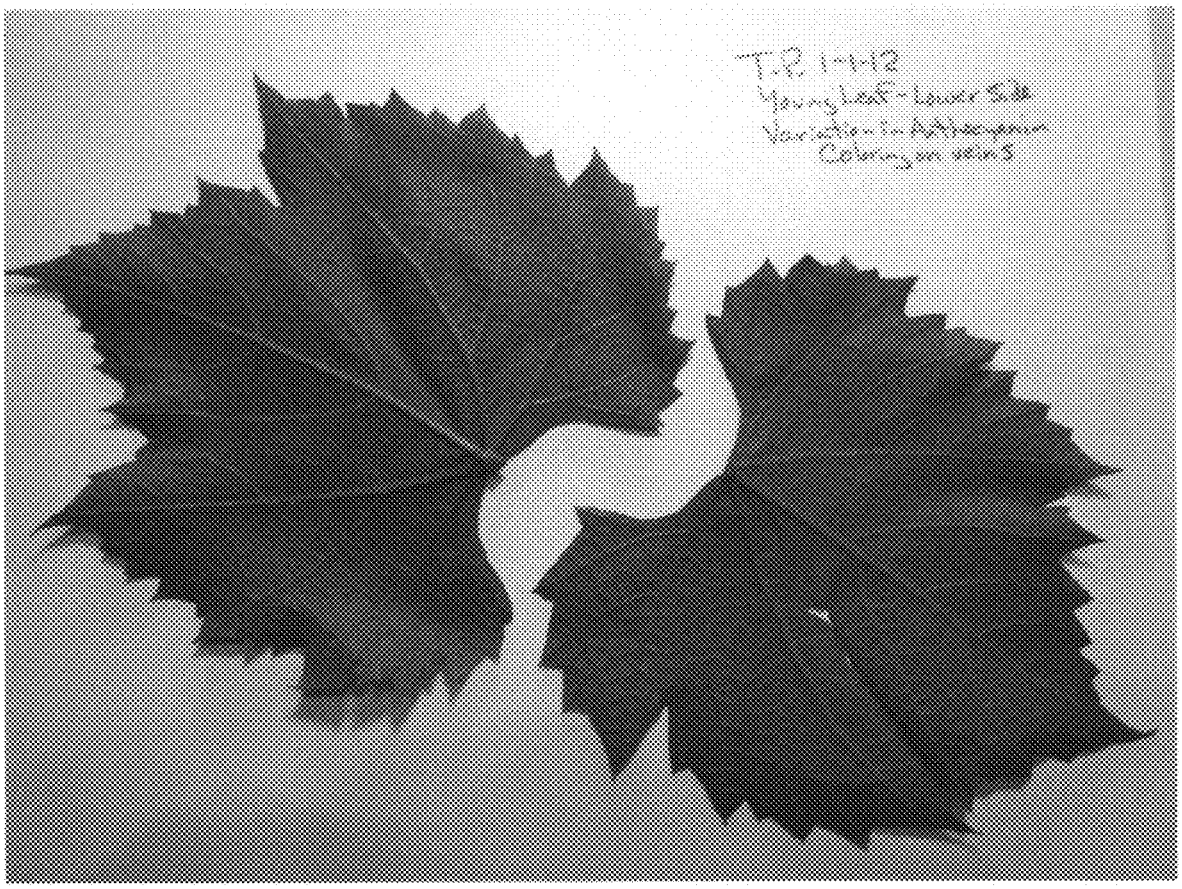
Figure 7:
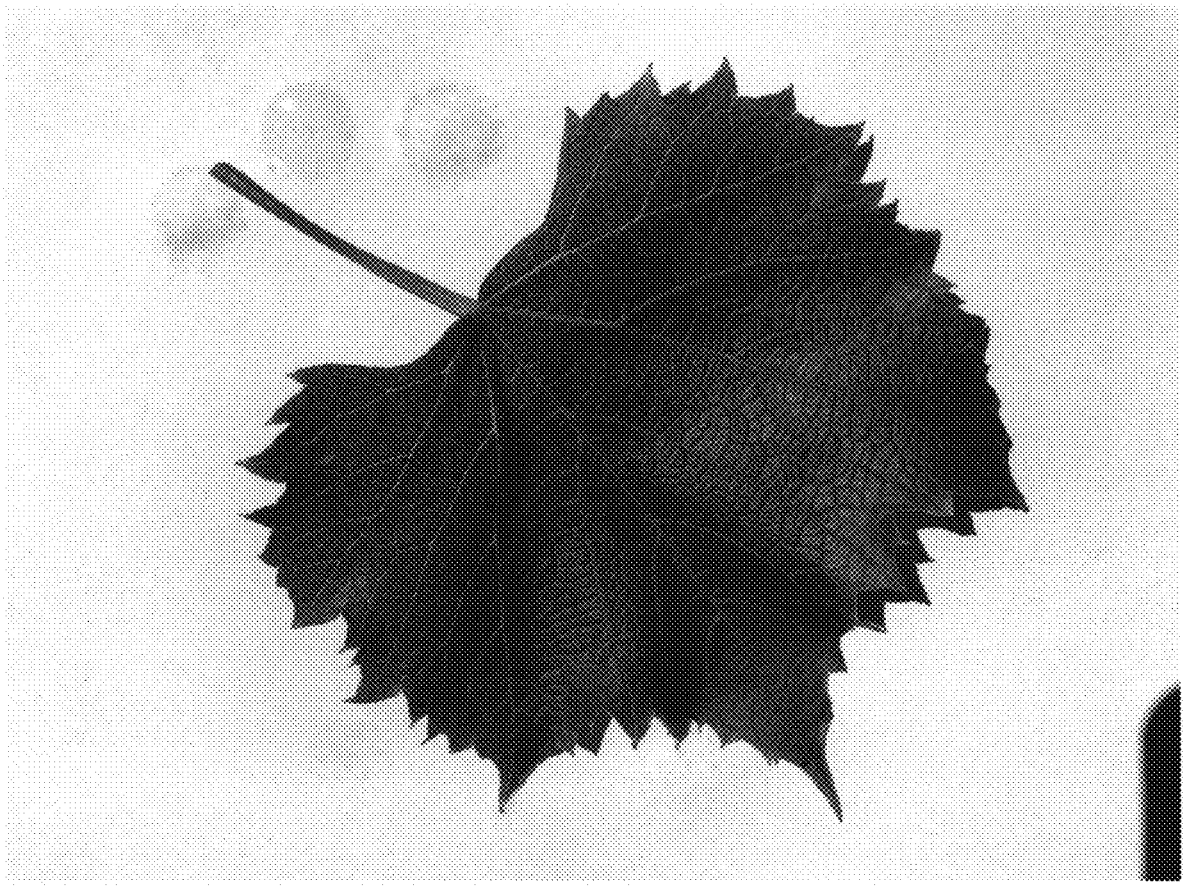
Figure 8:
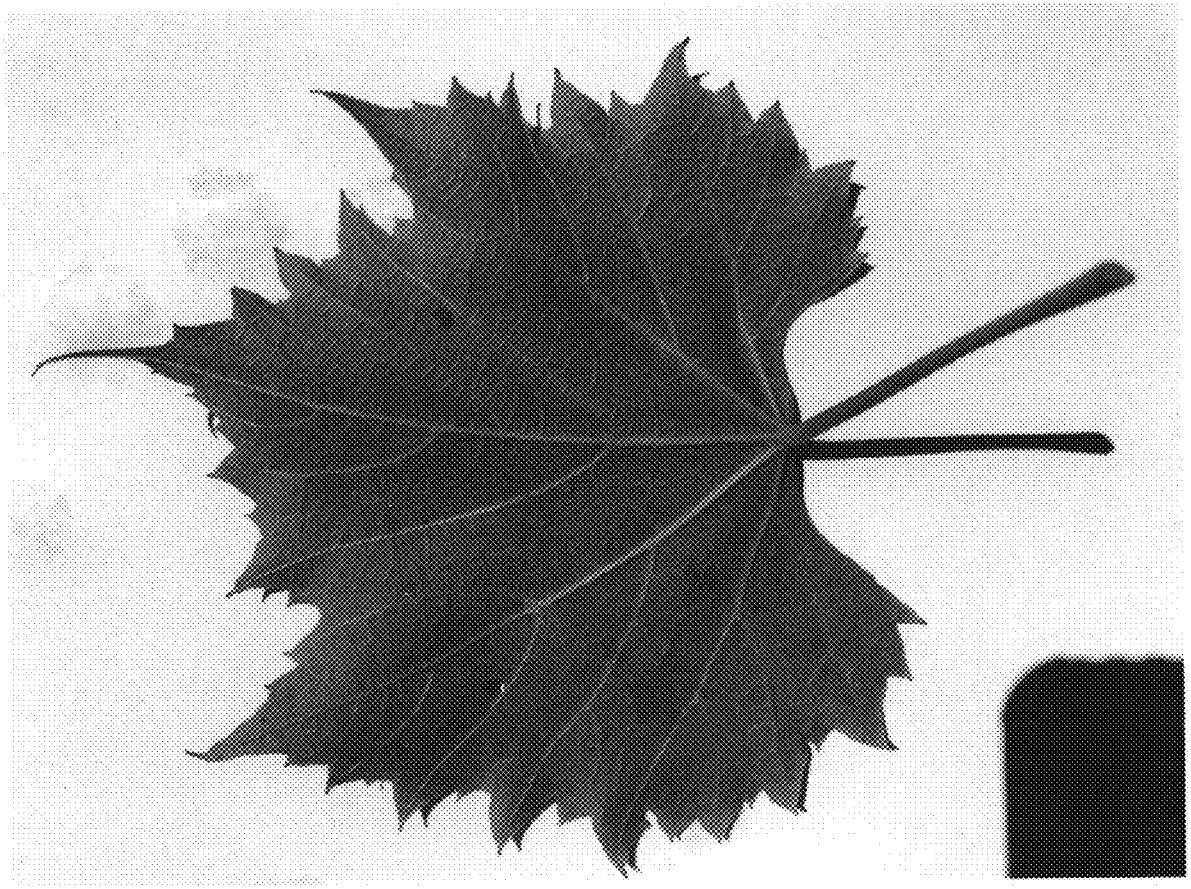
Figure 9:
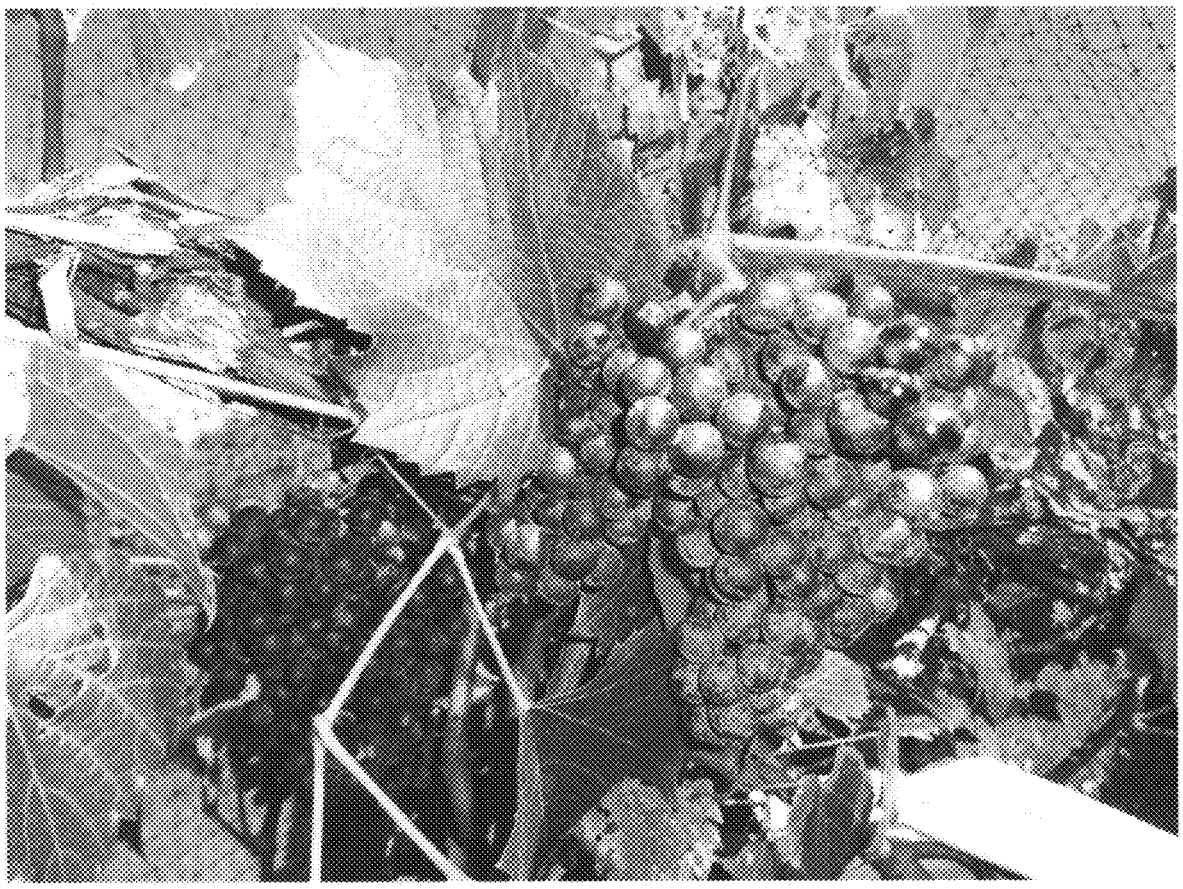
Figure 10:
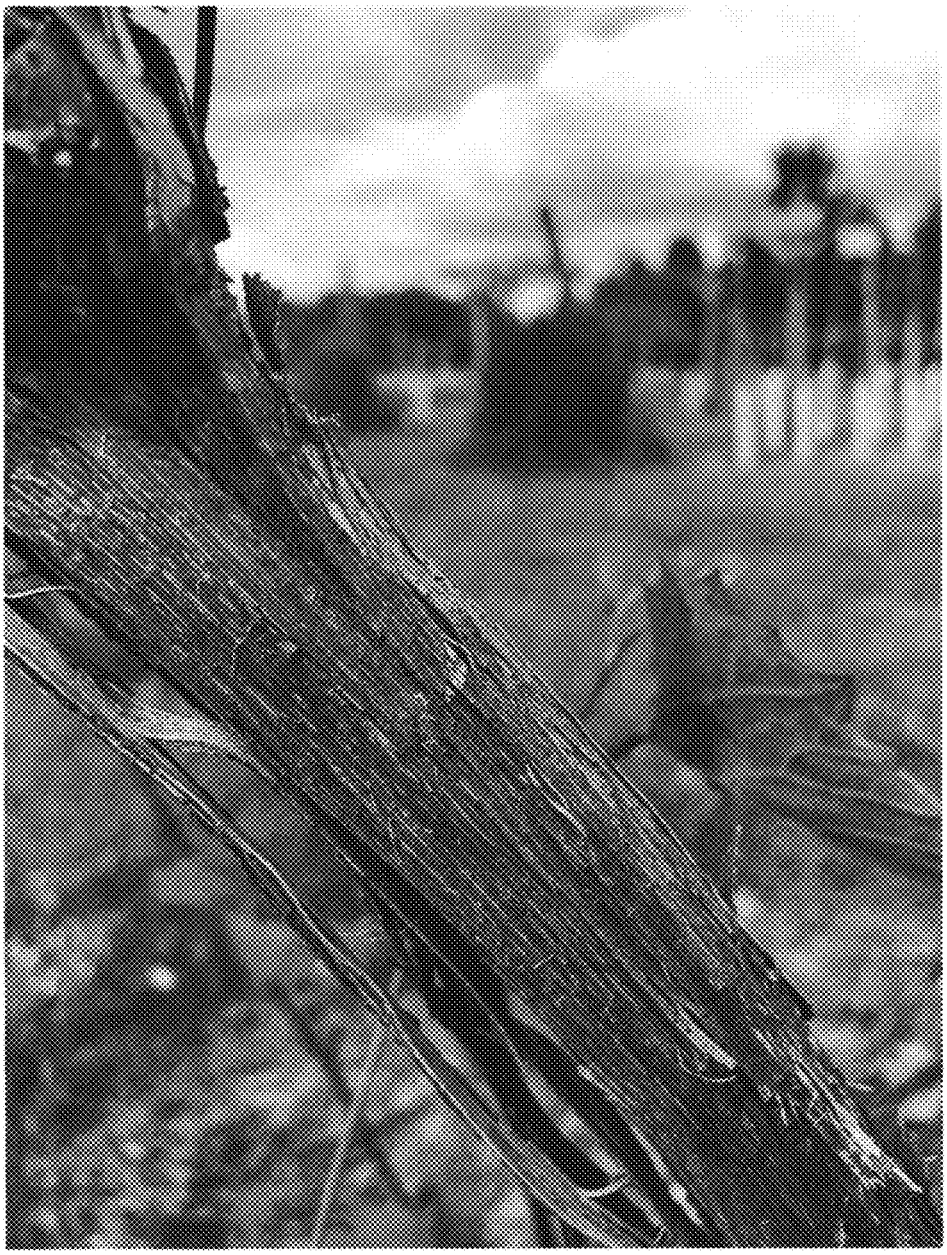

FIG. 1 shows a bud at first swell stage;
FIG. 2 shows a young shoot and leaves;
FIG. 3 shows an inflorescence;
FIG. 4 shows young tendrils;
FIG. 5 shows the vine, leaves, young shoots and inflorescences;

FIG. 6 shows young leaves;
FIG. 7 shows a mature leaf (upper surface);
FIG. 8 shows a mature leaf (lower surface);
FIG. 9 shows a typical cluster and leaf; and
FIG. 10 shows the trunk and bark.

DETAILED BOTANICAL DESCRIPTION OF THE VARIETY

The following-detailed botanical description is based on observations made during the 2016, 2018 and 2019 growing seasons at Hugo, Minn. of 2- and 3-year-old plants growing on their own roots. All colors are described according to The Royal Horticultural Society Colour Chart (Sixth edition). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average. "DDF 50" means "Degree Days Fahrenheit Base 50" and refers to accumulated heat units.

Vine:
- *Size*.—Medium.
- *Form*.—Intermediate between procumbent and upright.
- *Vigor*.—Moderate.
- *Timing of bud burst*.—6 May 2018 (50% first swell stage at 79.3 DDF 50) 30 Apr. 2015 (50% first swell stage at 90.3 DDF 50).
- *Productivity*.—4 tons per acre on average soil.
- *Trunk diameter*.—2.5 cm at 76 cm above the ground on 3 year old trunks.
- *Bark texture*.—Rough and slightly exfoliating.
- *Bark color*.—Brownish gray N200B.

Canes:
- *Diameter*.—6.6 mm (measured immediately distal to $4^{th}$ node).
- *Quantity*.—Typical pruning to 30 buds giving rise to 30 canes.
- *Bark color*.—Overwintered canes dark reddish orange 175B with very thin (0.2 mm) dark greyish reddish brown 200A lines running longitudinally.
- *Bark texture*.—Smooth.
- *Form*.—Round in cross section.
- *Node size*.—12.1 mm (measured at $4^{th}$ node).
- *Internode length*.—11.7 cm (measured between $3^{rd}$ and $4^{th}$ full node).
- *Number of tendrils per node*.—Tendrils are sparse in occurrence, with no regular repeating pattern.
- *Tendril thickness*.—1.5 to 2.0 mm.
- *Tendril length*.—Natural (uncurled) 10 cm; stretched 17.3 cm.
- *Tendril texture*.—Smooth.
- *Tendril color*.—Dark red 59A changing to strong yellow green 144C at the distal end 6 to 10 mm to the tip. Some slight strong yellow. green 144C mottling over the dark red 59A on the shade side of the tendril.

Flowers:
- *Fertility*.—Self-fertile.
- *Date of bloom*.—6 Jun. 2016 (approximately 479 DDF 50 from 1 January; 400 DDF 50 from 100% bud first swell to 50% caps off).
- *Number of inflorescences per shoot*.—2.
- *Numbers of flowers per inflorescence*.—636 to 935.
- *Shape of flower cluster*.—Conical, often with a wing.
- *Length of flower cluster*.—10 cm to 11.6 cm.
- *Width of flower cluster*.—5.5 cm to 7.0 cm.
- *Peduncle length*.—1.5 cm to 2.0 cm.
- *Peduncle diameter*.—3.3 mm.
- *Peduncle color*.—Dark red 183A.
- *Pedicel length*.—1.3 mm to 2.2 mm, average 1.8 mm.
- *Pedicel diameter*.—0.16 mm to 0.25 mm.
- *Pedicel color*.—Strong yellow green 144C.
- *Flower depth*.—5 mm.
- *Flower diameter*.—6 mm.
- *Filament length*.—3.2 mm to 4 mm, average 3.4 mm.
- *Filament color*.—Pale yellow green 157C.
- *Anther length*.—0.5 mm to 0.7 mm.
- *Anther color*.—Light yellow 11B.
- *Pistil length*.—1.7 to 2.7 mm.
- *Pistil color*.—Strong yellow green 144B, with varying amount (0% to 90%) of mottling with dark red 59A.
- *Stamen color*.—Pale yellow green 17C.
- *Stamen length*.—3.2 mm to 4 mm, average 3.4 mm.
- *Stamen quantity*.—5.
- *Cap color*.—Strong yellow green 144C with 0.5 mm dot of dark red 59A on top of cap in center.
- *Flower type*.—Hermaphroditic.

Young shoots (measured at flowering):
- *Openness of the tip*.—Closed.
- *Density of prostrate hairs on tip*.—Dense between veins, sparse on veins.
- *Anthocyanin coloration of prostrate hairs on tip*.—Bluish white N155A over green parts of the tip, to dark pink 182D over the red part of the tip.

Young leaf ($4^{th}$ distal leaf at flowering):
- *Shape*.—Circular.
- *Length*.—10.5 cm to 13.5, average 12.4 cm.
- *Width*.—11.0 cm to 13.2 cm, average 12.3 cm.
- *Color of upper upper surface*.—Moderate yellowish green 138A; in most cases, with dark red 59A anthocyanin pigmentation on primary veins and extending to minor veins.
- *Color of lower surface*.—Moderate yellowish green 1388, with dark red 59A anthocyanin coloring on the veins where petiole meets the primary vein. Coloring ranges from slight and confined to the first lateral veins branching off from the main vein where the petiole attaches, to quite prominent and showing on the major lateral veins and minor veins as well. In nearly all cases the main vein is free of anthocyanin coloring.
- *Density of prostrate hairs between main veins on lower side of blade*.—Very low to none.
- *Density of erect hairs on main veins on lower side of blade*.—Moderate.

Mature leaves (measured just before veraison):
- *Relative size*.—Medium.
- *Length*.—10.6 cm to 14 cm, average 12.7 cm.
- *Width*.—12.4 cm to 17.5 cm, average 13.9 cm.
- *Thickness*.—0.51 mm to 0.58 mm, average 0.54 mm.
- *Shape*.—Circular.
- *Margin*.—Erose to serrate.
- *Base*.—Cordate.
- *Color*.—Upper surface — Moderate yellowish green 138A.
- *Color*.—Lower surface — Strong yellow green 144A.

*Anthocyanin coloration of main veins on upper surface*.—Dark red 59A starting at the petiole and showing for about 75% of the extent of the veins.

*Texture*.—Upper surface — Mostly hairless between veins; moderately corrugated; moderately dense prostrate hairs on major veins.

*Texture*.—Lower surface — Hairless between veins; veins mostly hairless except for moderate number of erect hairs on sides of veins and slight prostrate hairs on top of veins.

*Number of lobes*.—3.

*Terminal lobe*.—Form — Pointed, rectilinear.

*Lateral sinus depth*.—Left 1.4 cm to 2.5 cm, average 2.1; Right 1.0 cm to 2.8 cm, average 2.1.

*Lateral sinus shape*.—Very shallow asymmetrical flattened U-shape.

*Relative arrangement of lateral sinus lobes*.—Open, not touching.

*Petiole color*.—Moderate reddish purple 58A over strong yellow green N144C.

*Petiole sinus depth*.—1.0 cm to 2.0 cm, average 1.7 cm.

*Petiolar sinus shape*.—U-shaped.

*Relative arrangement of petiolar sinus lobes*.—Open, not touching.

*Petiole sinus limited by veins*?.—Yes.

*Petiole length*.—5.0 cm to 7.5 cm, average 6.4 cm.

*Petiole diameter*.—2.1 mm to 3.2 mm, average 2.5 mm.

*Length of middle vein*.—10.7 to 13.7 cm, average 12.7 cm.

*Ratio of petiole length/length of middle vein*.—0.41 to 0.59, average 0.51.

*Length of teeth*.—0.6 to 1.5 cm, average 0.95 cm.

*Width of teeth*.—0.7 to 1.5 cm, average 1.0 cm.

*Ratio of length/width of teeth*.—0.8 to 1.2, average 0.9.

Mature tendrils (measured after veraison):

*Quantity*.—Sparse; no regular repeating pattern.

*Thickness*.—1.5 mm to 2.0 mm.

*Length*.—Natural (uncurled) 10 cm; stretched 17.3 cm.

*Texture*.—Smooth.

*Color*.—Dark red 59A changing to strong yellow green 144C at the distal end 6 mm to 10 mm to the tip; also some slight strong yellow green 144C mottling over the dark red 59A on the shade side of the tendril.

Shoot (measured at flowering):

*Attitude* (*before tying*).—52 degree angle relative to the cane.

*Color of dorsal side of internode* (*well-illuminated*).—Moderate red 183 with longitudinal stripes of dark red 59A.

*Color of ventral side of internode* (*without direct sunlight*).—Strong yellowish green 141C.

*Density of erect hairs on internodes*.—Not present on upper side; sparse on under side.

*Number of consecutive tendrils*.—Usually 2 to 3 consecutive, occasionally 4 consecutive, followed by one node with no tendril, followed again by a node with a tendril.

*Length of tendrils*.—10 cm to 13.5 cm, average 11.4 cm.

*Thickness of tendril*.—1.1 mm to 1.4 mm, average 1.3 mm.

*Form of tendril*.—Most branch one time, halfway up the tendril; a few branch two times, once halfway up, and once at the end of the first branch.

*Color of young tendril*.—Strong yellow green 144B, with dark purplish red N79B on one side below the point where the tendril branches.

*Color of mature tendril*.—Moderate red 183D from the proximal end, turning to strong greenish yellow 151A at the branching point.

Fruit:

*Veraison* (100% *of berries colored blue*).—17 Aug. 2016.

*Maturity date*.—Early-Mid September in Hugo, Minn. (45.1600° N, 92.9933° W); 5 Sep. 2018 (2482 DDF 50); 24 Sep. 2015 (2479 DDF 50); 9 days earlier than 'Crimson Pearl'.

*Shape*.—Roundish.

*Length*.—11.2 mm to 13.1 mm, average 12.0 mm.

*Width*.—11.0 mm to 13.4 mm, average 12.2 mm.

*Weight*.—1.05 g.

*Relative size*.—About the same size as 'Petite Pearl' (not patented); smaller than 'Crimson Pearl' (U.S. Plant Pat. No. 30,263) and 'Verona' (U.S. Plant Pat. No. 30,631).

*Brix*.—23 degrees

*Skin thickness*.—0.89 mm to 0.98 mm, average 0.92 mm.

*Skin color*.—Violet blue 98A overlaid with greyish purplish blue 103A.

*Flesh color*.—Pale yellow 160D.

*Tendency to crack*.—No tendency to crack, even under wet conditions.

*Flesh texture*.—Slipskin.

*Number of berries per cluster*.—72 to 117, average 93.8.

*Juice production*.—15.45 lbs. (about 7 kg) fruit produces 1 gallon (3.78 L).

Juice:

*Juice color*.—Dark red 59A.

*Flavor*.—Fruity, slightly herbaceous.

*Seed length*.—5.3 mm.

*Seed width*.—3.8 mm.

*Seed thickness*.—3.2 mm.

*Seed shape*.—Pyriform.

*Seed color*.—Moderate yellowish brown N199C; mottled with strong yellowish brown N199D.

*Anthocyanin coloration on seeds*.—Very slight; a few dots of dark red 59A.

Cluster:

*Overall shape*.—Conical with 2 wings, sometimes 3 wings.

*Relative size*.—Larger than 'Petite Pearl' and 'Crimson Pearl'.

*Weight*.—113 g to 238 g, average 163 g.

*Length*.—11.5 cm to 17 cm, average 13.8 cm.

*Width*.—8 cm to 14 cm, average 10.8 cm.

*Peduncle length*.—2.5 cm to 2.9 cm, average 2.7 cm.

*Peduncle thickness*.—3.7 mm to 4.3 mm, average 4 mm.

*Pedicel length*.—5 mm, very consistent.

*Pedicel thickness*.—2.9 mm to 3.8 mm, average 3.3 mm.

*Market use*.—Wine production.

*Storage and shipping quality*.—Poor.

*Disease resistance/susceptibility*.—High resistance to downy mildew (*Plasmopara viticola*) and powdery mildew (*Erysiphe necator* (Schw.) Burr.); Good resistance to black rot (*Guignardia bidwellii*). In humid climates such as southern Minnesota, quite susceptible to trunk diseases such as *Botryosphaeria*. Manageable by more frequent replacement of trunks, cultivation of younger trunks, and good pruning sanitation.

The invention claimed is:

1. A new and distinct grape plant substantially as described and illustrated herein.

* * * * *